(12) United States Patent
Voothkoor et al.

(10) Patent No.: US 10,721,346 B2
(45) Date of Patent: Jul. 21, 2020

(54) INTEGRATED PLATFORM FOR AGGREGATING CONTEXT INFORMATION

(71) Applicant: NCR Corporation, Atlanta, GA (US)

(72) Inventors: Nikitha Voothkoor, Secunderabad (IN); Anusha Amaravadi, Suryapet (IN); Vishal Kumar Vasi, Tirumalgiri (IN); Adilakshml Kameshwari Sistla, Hyderabad (IN); Haritha Supuri, Nizampet (IN)

(73) Assignee: NCR Corporation, Atlanta, GA (US)

( * ) Notice: Subject to any disclaimer, the term of this patent is extended or adjusted under 35 U.S.C. 154(b) by 0 days.

(21) Appl. No.: 16/158,741

(22) Filed: Oct. 12, 2018

(65) Prior Publication Data
US 2020/0120197 A1    Apr. 16, 2020

(51) Int. Cl.
| H04W 4/00 | (2018.01) |
| H04M 1/725 | (2006.01) |
| G06Q 30/02 | (2012.01) |
| G16H 80/00 | (2018.01) |
| G06Q 50/00 | (2012.01) |

(52) U.S. Cl.
CPC .... H04M 1/72566 (2013.01); G06Q 30/0224 (2013.01); G06Q 30/0252 (2013.01); G06Q 50/01 (2013.01); G16H 80/00 (2018.01)

(58) Field of Classification Search
CPC ............................ H04W 4/16; H04M 1/72566
See application file for complete search history.

(56) References Cited

U.S. PATENT DOCUMENTS

| 2013/0166360 | A1* | 6/2013 | Kshetramade | G06Q 30/02 705/14.1 |
| 2013/0288778 | A1* | 10/2013 | Johnson | G07F 17/3204 463/25 |
| 2013/0325605 | A1* | 12/2013 | Callaghan | G06Q 30/02 705/14.53 |
| 2014/0067544 | A1* | 3/2014 | Klish | G06Q 30/02 705/14.66 |
| 2014/0089099 | A1* | 3/2014 | Money | G06F 3/0485 705/14.66 |
| 2014/0149193 | A1* | 5/2014 | DeLuca | G06Q 30/0207 705/14.5 |
| 2018/0032757 | A1* | 2/2018 | Michael | G06F 21/6245 |

* cited by examiner

Primary Examiner — Omoniyi Obayanju
(74) Attorney, Agent, or Firm — Schwegman, Lundberg & Woessner

(57) ABSTRACT

Events and offers based on context is provided by determining an event based on a social media footprint, determining a group of people associated with the event based on the social media footprint, generating an offer based on the group of people and the event; and causing the offer to be displayed to at least one of the group of people.

13 Claims, 13 Drawing Sheets

INTEGRATED PLATFORM FOR AGGREGATING CONTEXT INFORMATION

BACKGROUND

Often decisions for determining services or products to offer to an individual are based on individual information. Often the goods and services that can be offered to an individual are limited by the information that can be determined from the individual. Additionally, often the decisions to purchase a good or service is limited to an individual decision.

Moreover, often a calendar has become a central organization tool for people's lives. The information available to an individual on their calendar is often limited to the information that is input by the individual or that is sent to the individual from other people, e.g., meeting requests.

SUMMARY

In various embodiments, methods and an integrated platform for aggregating context information are presented.

According to an embodiment, a method for contextualized events, groups of people, and offers is provided. Specifically, in an embodiment, determining an event based on a social media footprint, determining a group of people associated with the event based on the social media footprint, generating an offer based on the group of people and the event, and causing the offer to be displayed to at least one of the group of people.

According to an embodiment, a method for contextualized events with automatic calendar updates is provided. Specifically, in an embodiment, sending requests for information to a social media site in accordance with an application program interface of the social media site, receiving information from the social media site, determining an event and a group of people associated with the event based on the information from the social media site, and sending calendar update messages to a calendar of each of the people in the group in accordance with an application program interface of the calendar.

DETAILED DESCRIPTION

Figure 1:
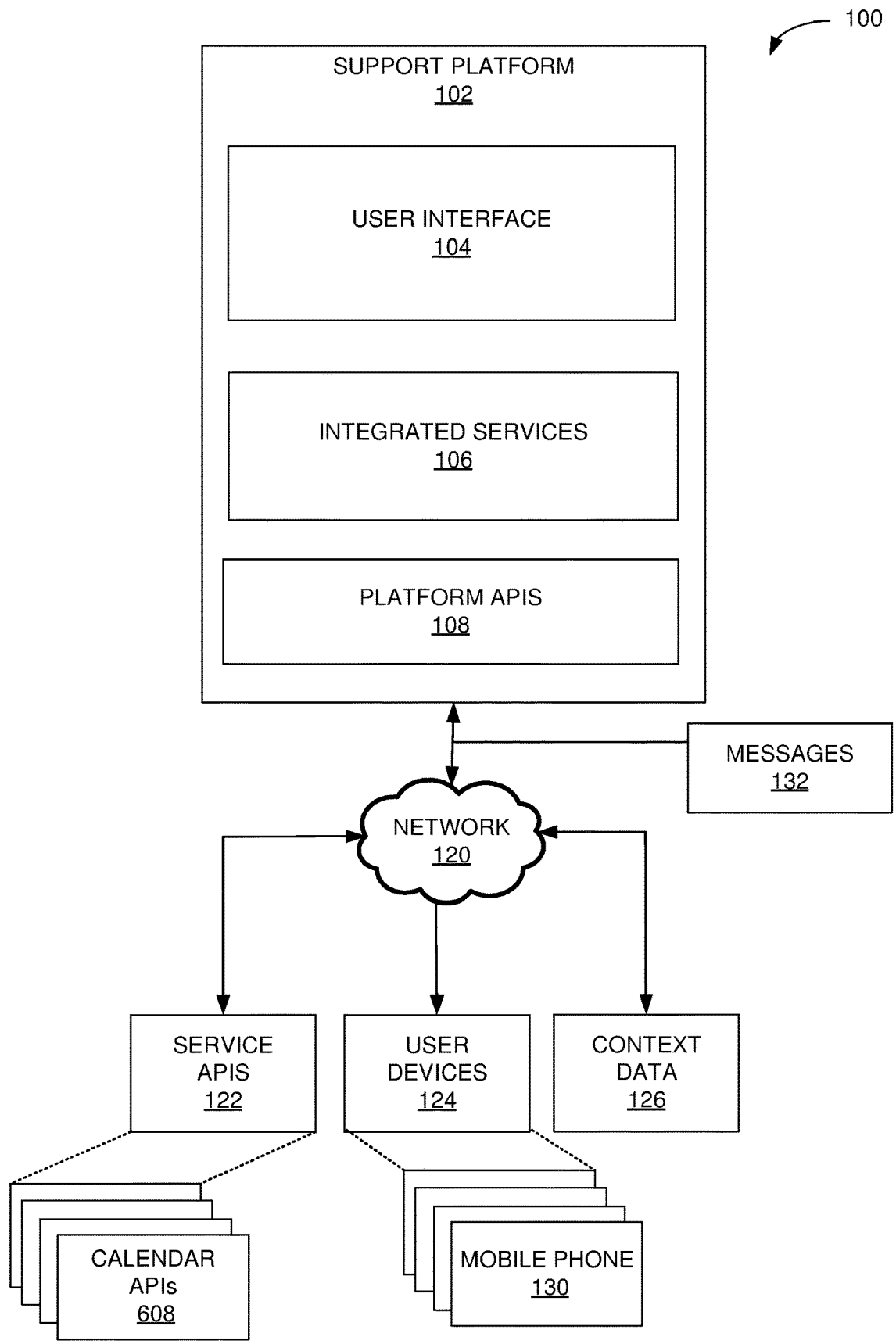
FIG. 1 is an integrated platform for aggregating context information in accordance with some embodiments.

FIG. 1 is an integrated platform for aggregating context information 100 in accordance with some embodiments. Illustrated in FIG. 1 is support platform 102, network 120, messages 132, service APIs 122, user devices 124, and context data 126.

The support platform 102 may be a cloud-based technology platform, e.g., the support platform 102 may be implemented on one or more computer servers, e.g., 1500. The support platform 102 may be an Omni-Channel Decision Support Platform (ODSP)™. The support platform 102 may include user interface 104, integrated services 106, and platform APIs 108. The user interface 104 may include one or more modules for interaction, e.g., to interact with user devices 124, context data 126, and/or service APIs 122. The user interface 104 may be configured to interact via the network 120. The user interface 104 may be configured to generate and/or decode one or more of the messages 132.

Figure 4:
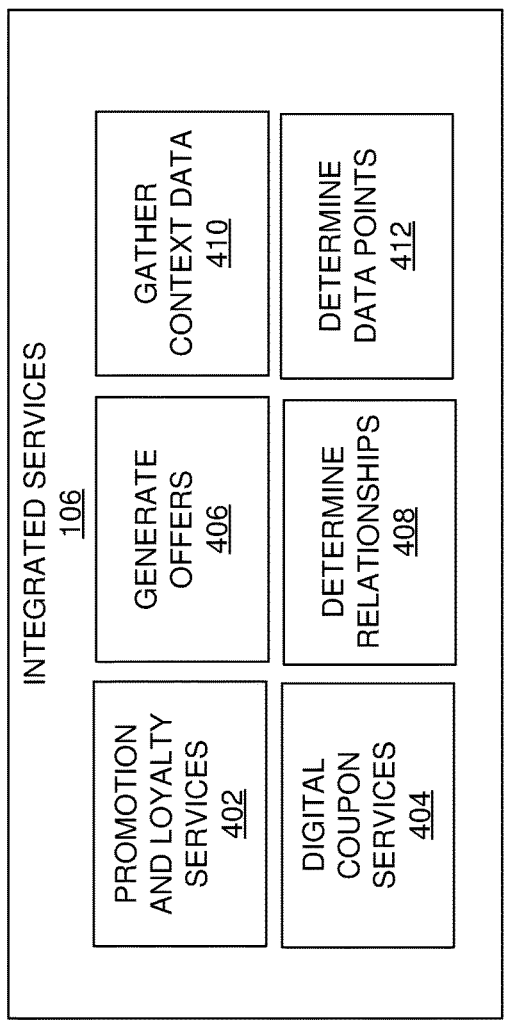
FIG. 4 illustrates integrated services in accordance with some embodiments.

The integrated services 106 may be services such as disclosed in conjunction with FIG. 4, e.g., promotion and loyalty services 402, digital coupon services 404, etc. The integrated services 106 may be configured to operate with the user interface 104 and platform APIs 108. The integrated service 106 may be configured to interact with the user devices 124, service APIs 122, and context data 126. The integrated services 106 may be configured to operate via the network 120. The integrated services 106 may be configured to generate and/or decode one or more of the messages 132.

Figure 2:
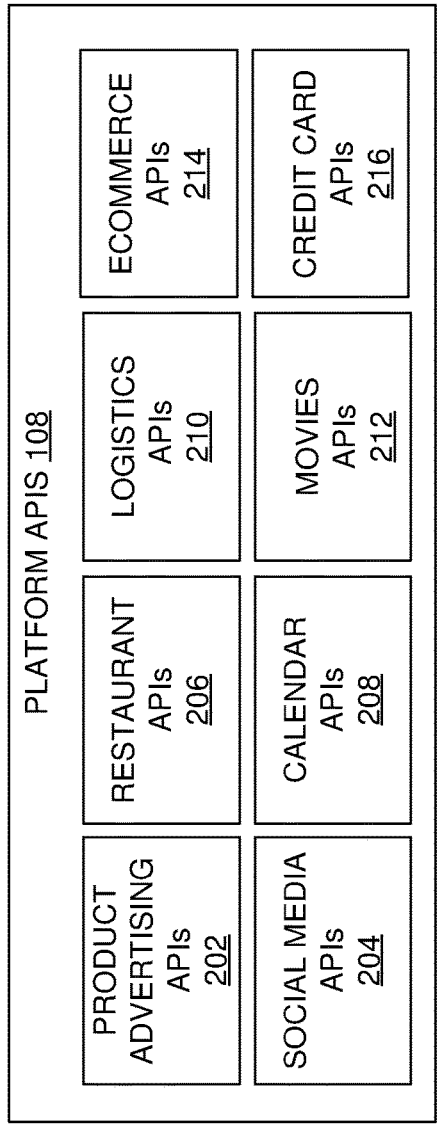
FIG. 2 illustrates platform APIs in accordance with some embodiments.

The platform APIs 108 may be APIs such as disclosed in conjunction with FIG. 2, e.g., product advertising APIs 202, social media APIs 204, etc. The platform APIs 108 may be configured to interact with the user devices 124, service APIs 122, and context data 126. The platform APIs 108 may be configured to operate via the network 120. The platform APIs 108 may be configured to generate and/or decode one or more of the messages 132. In some embodiments, a platform API 108 may be configured to operate with a corresponding service API 122. For example, a calendar API 208 (e.g., Google Calendar®) may be configured to operate with calendar APIs 308. The platform APIs 108 may be configured to access websites via a browser.

Figure 5:
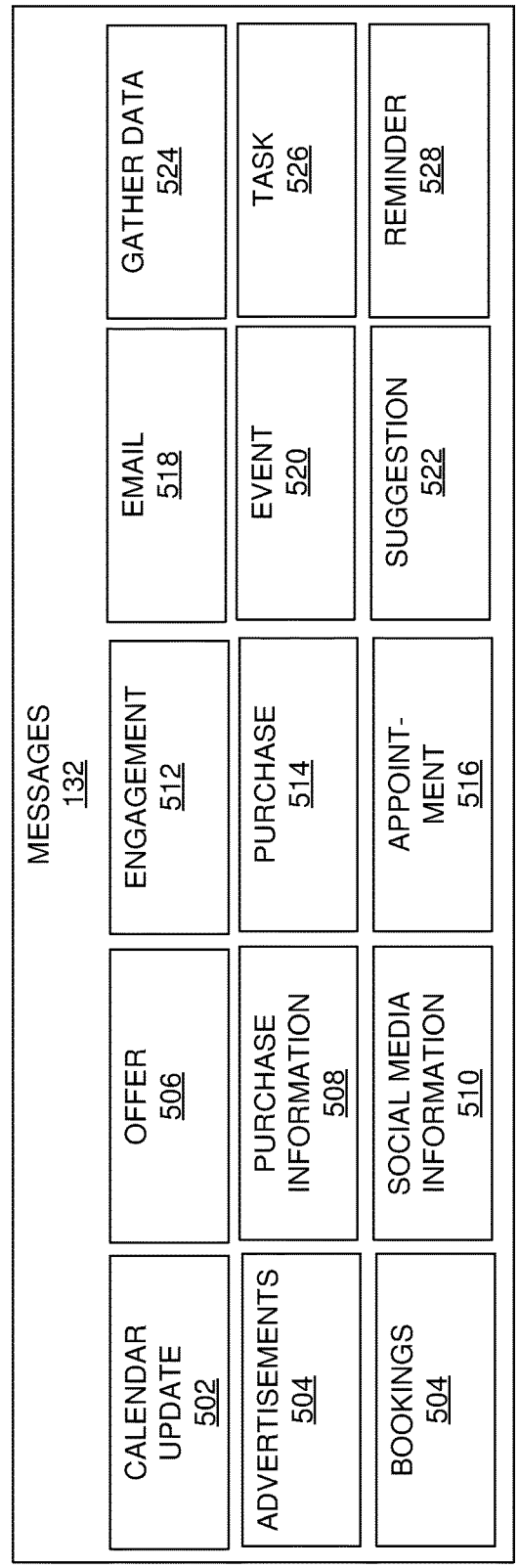
FIG. 5 illustrates messages in accordance with some embodiments.

The messages 132 may be messages 132 as disclosed in conjunction with FIG. 5, e.g., calendar updates 502, advertisements 504, bookings 504, etc. The network 120 may be a network such as a local area network, the internet, or another type of network.

Figure 3:
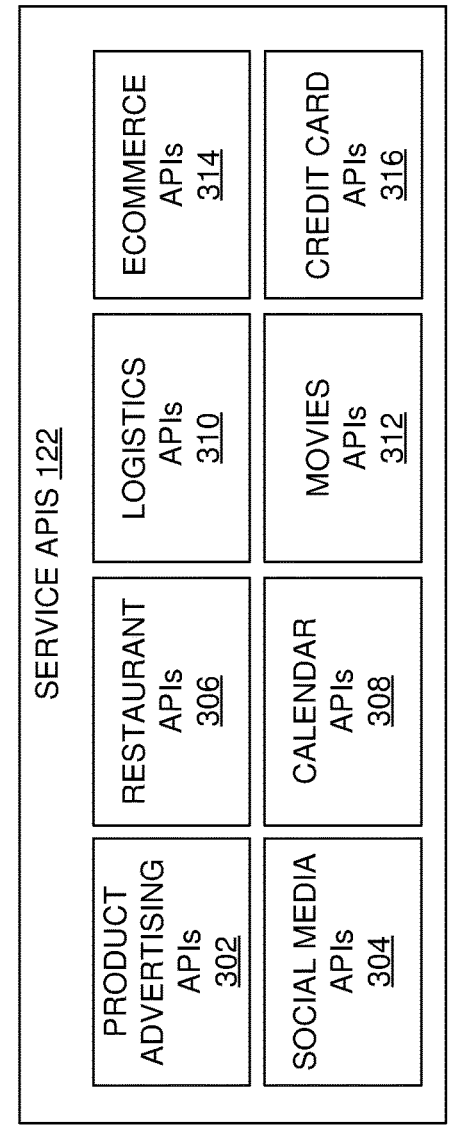
FIG. 3 illustrates service APIs in accordance with some embodiments.

The service APIs 122 may be APIs as disclosed in conjunction with FIG. 3, e.g., product advertising APIs 302, social media APIs 304, etc. The service APIs 122 may provide access to one or more service or product websites or computer systems (not illustrated). The service APIs 122 may be configured to operate via the network 120. The service APIs 122 may be configured to generate and/or decode one or more of the messages 132.

The user devices 124 may comprise a mobile phone 130, desktop computer, laptop, portable digital assistants (PDAs), smart phones, tablets, ultra books, netbooks, laptops, multi-processor systems, microprocessor-based or programmable consumer electronics, game consoles, set-top boxes, or another communication device that may access the network 120. The user devices 124 may host one or more of the service APIs 122. For example, a mobile phone 130 may include service APIs 122 such as calendar APIs 308, which may communicate with the platform APIs 112, e.g., calendar APIs 208. The user devices 124 may have local storage. The user devices 124 may host one or more modules (e.g., a calendar module) that stores data across the network 120.

Figure 6:
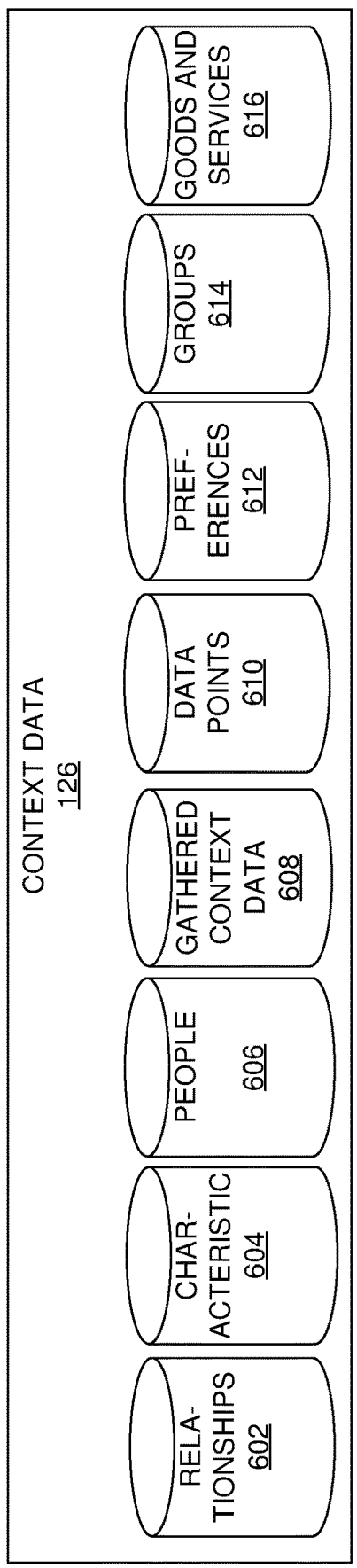
FIG. 6 illustrates context data in accordance with some embodiments.

The context data 126 may comprise context data 126 as disclosed in conjunction with FIG. 6, e.g., relationships 602, characteristics 604, etc. The context data 126 may be gathered using the platform APIs 112 to gather data from calendars (e.g., using calendar APIs 208), social media websites (e.g., ecommerce APIs 214), purchase histories (e.g., credit card APIs), etc.

FIGS. 2-6 are disclosed in conjunction with one another. FIG. 2 illustrates platform APIs 108 in accordance with some embodiments. The platform APIs 108 may include one or more APIs that may be used to access external systems. The platform APIs 108 may include product advertising APIs 202, social media APIs 204, restaurant APIs 206, calendar APIs 208, logistics APIs 210, movies APIs 212, ecommerce APIs 214, credit card APIs 216, etc. The platform APIs 108 may be configured to communicate with service APIs 122 across the network 120. The platform APIs 108 may be configured to generate and/or decode one or more of the messages 132.

FIG. 3 illustrates service APIs 122 in accordance with some embodiments. Service APIs 122 may reside on systems accessible to the support platform 102 via the network 120. The service APIs 122 may include one or more APIs that may be provide services that enable the platform APIs 108 to access the services, e.g., on websites or user devices 124.

The product advertising APIs 202 may be configured to communicate with product advertising APIs 302. The product advertising APIs 302 may provide APIs for performing functions related to product advertising, e.g., retrieving product advertisements based on dates and desired services and/or products, and sending product advertisements to the user devices 124. The product advertising APIs 202 may be configured to access commercial websites, e.g., Amazon®, Flipkart®, etc.

The social media APIs 204 may be configured to communicate with social media APIs 304. The social media APIs 304 may provide APIs for performing functions related to social media, e.g., retrieve data related to information stored regarding people 606 on the social media site, e.g., likes, posts, friends, etc. The social media APIs 204 may include APIs to access medical professionals or other professionals' websites or services, e.g., access to appointments and services provided by the professionals.

The restaurant APIs 206 may be configured to communicate with restaurant APIs 306. The restaurant APIs 306 may provide APIs for performing functions related to restaurants, e.g., making a reservation, determining availability, determining menus, ordering food, etc. The restaurant APIs 206 may be configured to access commercial websites, e.g., Google Restaurant®, Zomato®, etc.

The calendar APIs 208 may be configured to communicate with calendar APIs 308. The calendar APIs 308 may provide APIs for performing functions related to calendars, e.g., making appointments, retrieving appointments, setting reminders, etc.

The logistics APIs 210 may be configured to communicate with logistics APIs 310. The logistics APIs 310 may provide APIs for performing functions related to logistics, e.g., booking taxis, booking car services, determining rates, determining availability, etc. The logistics APIs 210 may be configured to access commercial websites, e.g., Flight®, TrailAPI®, Expedia®, etc.

The movies APIs 212 may be configured to communicate with movies APIs 312. The movies APIs 312 may provide APIs for performing functions related to movies, e.g., booking movie reservations, determining movies playing, determining movie playing times, etc. The movies APIs 212 may be configured to access commercial websites, e.g., BookmyShow®, MeraEvents®, etc.

The ecommerce APIs 214 may be configured to communicate with ecommerce APIs 314. The ecommerce APIs 314 may provide APIs for performing functions related to ecommerce, e.g., determining special offers, requesting pricing for products or service, requesting products or services availability, purchasing a product or service, making an offer for a product or service, etc.

The credit card APIs 216 may be configured to communicate with credit card APIs 316. The credit card APIs 316 may provide APIs for performing functions related to credit cards, e.g., determining special offers, requesting purchase history, balances, credit limit, purchasing items using a credit card, etc. The APIs illustrated in platform APIs 108 and service APIs 122 are non-limiting examples of APIs that may be used to access products and services across the network 120.

FIG. 4 illustrates integrated services 106 in accordance with some embodiments. Integrated services 106 may include promotion and loyalty service 402, digital coupon services 404, digital coupon services 406, generate offers 406, determine relationships 408, gather context data 410, and determine data points 412. The integrated services 106 illustrated in FIG. 4 are non-limiting examples of integrated services that may be used by the support platform 102.

The promotion and loyalty services 402 may use platform APIs 108 to promote products and/or services and offer a loyalty benefits to users on their user devices 124. The digital coupon services 404 may use platform APIs 108 to offer, redeem, search for, and/or promote coupons. The generate offers 406 may use platform APIs 108 and context data 126 to determine offers, events, etc., and make the offers, events, etc. to users on user devices 124. Determine relationships 408 may use platform APIs 108 and context data 126 to determine relationships between people 606 or users. The determine relationships 408, e.g., may search for data on social media using social media APIs 204 and in calendars using the calendar APIs 208. The determine relationships 408 may store the data in context data 126 and search through the context data 126 to determine relationships between people 606 or users, e.g., friends, relatives, father, son, daughter, mother, supervisor, etc.

Gather context data 410 may use platform APIs 108 to gather context information. For example, gather context data 410 may use credit card APIs 216 to gather purchase history of people 606, ecommerce APIs 214 to gather purchase history of people 606, etc. Determine data points 412 may determine data points 610 such as tasks, events, reminders, notifications, meetings, etc., a person needs to perform, offers for one or more people 606, events for one or more people 606, appointments for one or more people 606, etc.

FIG. 5 illustrates messages 132 in accordance with some embodiments. The messages 132 may be messages that are generated and/or decoded by the platform APIs 108, service APIs 122, user devices 124, user interface 104, and/or integrated service 106, and which may be sent across the network 120.

Example messages 132 include calendar updates 502, advertisements 504, bookings 504, offer 506, purchase information 508, social media information 510, engagement 512, purchase 514, appointment 516, email 518, event 520, suggestion 522, gather data 524, task 526, and reminder 528.

A calendar update message 502 may include one or more updates for a calendar. An advertisements message 504 may include one or more advertisements, e.g., for presentation to a person 606 or user on a user device 124. A bookings message 504 may include one or more bookings requests and/or confirmations. An offer message 506 may include one or more offers, e.g., for a movie, car rental, an offer to pay a certain amount for a product, etc. The offer message 506 may include notifications, e.g., regarding necessities such as health checkups, clothing, vaccines, etc. A purchase information message 508 may include information regarding a purchase that has occurred, etc. A social media information message 510 may include information from a social media site, information to be posted to a social media site, etc. An engagement message 512 may include information for an engagement, a message to set an engagement to a calendar, etc.

A purchase message 514 may include an instruction to purchase a good or service, information regarding a purchase, etc. An appointment message 516 may include information regarding an appointment, an instruction to make an appointment, etc. An email message 518 may include an email, an instruction to send an email, etc. An event message 520 may include an event, an instruction to cancel an event, an instruction to make an event, etc.

A suggestion message 522 may include a suggestion to be presented to a person 606 or user on a user device 124. A gather data message 524 may include an instruction to gather data, information gathered, etc. A task message 526 may include an instruction to add a task to a calendar, information regarding a task, etc. A reminder message 528 may include an instruction to add a reminder to a calendar, an instruction to display a reminder to a person or user, etc.

FIG. 6 illustrates context data 126 in accordance with some embodiments. Context data 126 may be data that is available to the support platform 102 across the network 120 and/or may be available locally. Context data 126 may include relationships 602, characteristics 604, people 606, gather context data 608, data points 610, preferences 612, groups 614, and goods and services 616. The relationships 602 may be relationships among the characteristics 604, people 606, gathered context data 608, data points 610, preferences 612, groups 614, and/or goods and services 616. For example, relationships 602 may include family relationships of people as well as favorite stores of people 606.

Characteristics 604 may include characteristics of people 606 or other data, e.g., age, number of children, profession, etc. People 606 may be people and may include information such as social media pages, shopping sites, etc. Person, individual, user, etc., may be used interchangeably in accordance with some embodiments. Gather context data 608 may include information about people 606 and goods and services 616, e.g., data from social media sites such as likes, purchase history of people, etc. Data points 610 may include information such as birthdays, anniversaries, family events, discounted products, alerts (formal and informal), appointments (e.g., travel, medical, entertainment), etc. Preferences 612 may include information regarding people 606 and good and services 616 such as type of car to rent, types of activities or presents preferred, types of meals preferred, etc.

Groups 614 may include groups of people 606 that indicates some type of relationships for the people 606, e.g., families, work colleagues, etc. Goods and services 616 may list good and services, e.g., car services, restaurants, etc., and may include associations with people 606 or other data. The different databases or stores of data in the context data 126 may overlap. Additional data may be present in context data 126.

Figure 7:
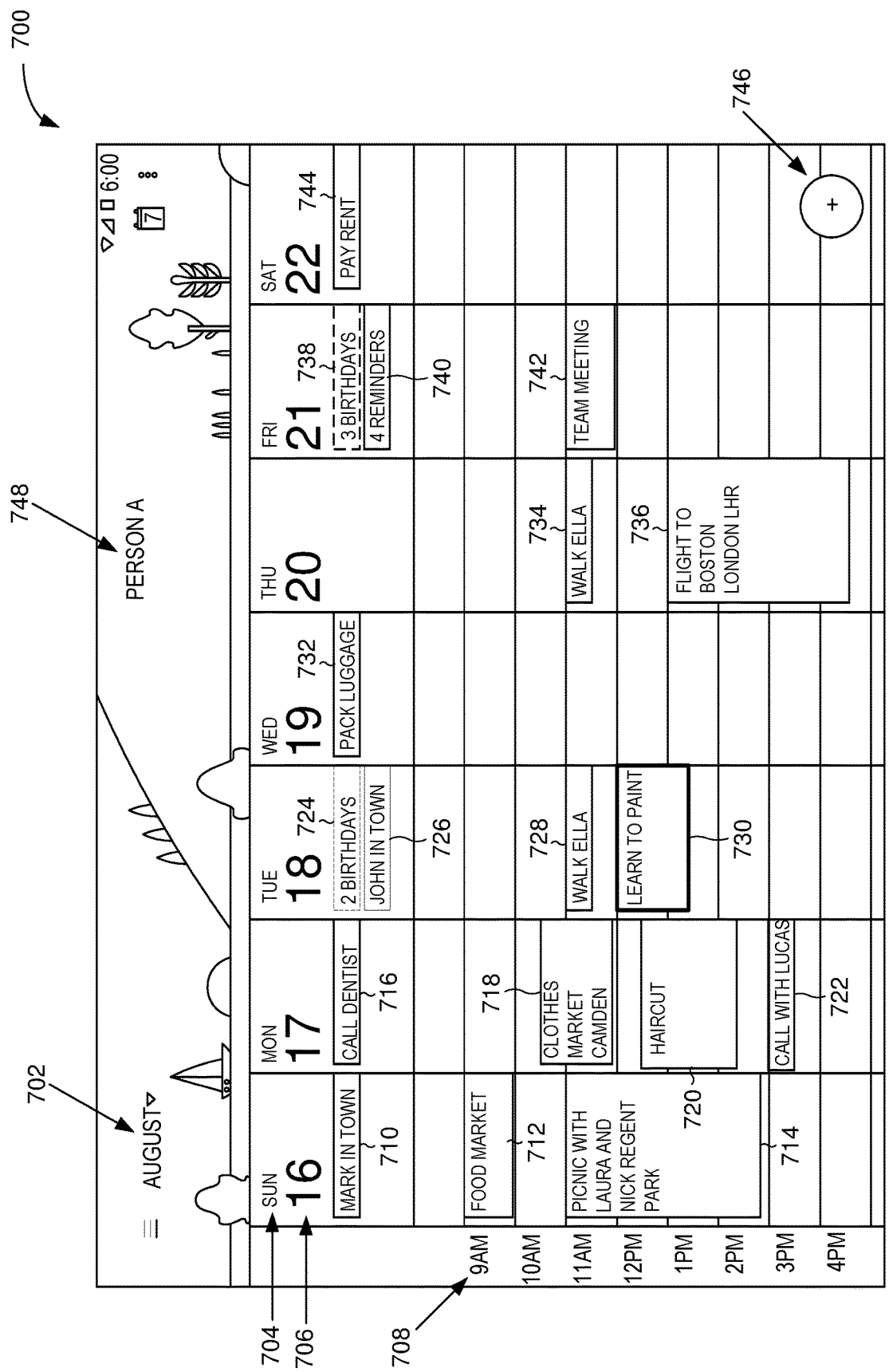
FIG. 7 illustrates an events and engagement view of a calendar in accordance with some embodiments.

FIG. 7 illustrates an events and engagement view of a calendar 700 in accordance with some embodiments. The events and engagement calendar 700 may belong to person A 748 (e.g., a person of people 606) and may be a Google Calendar®. Illustrated in FIG. 7 is August 702, day of week 704, date 706, time 708, mark in town 710, food market 712, picnic with Laura and Nick 714, call dentist 716, clothes market 718, haircut 720, call with Lucas 722, 2 birthdays 724, John in town 726, walk Ella 728, learn to paint 730, pack luggage 732, walk Ella 734, flight to Boston 736, 3 birthdays 738, 4 reminders 740, team meeting 742, pay rent 744, add engagement 746, and person A 748. Some of the events and engagements 710, 712, 714, 716, 718, 720, 722, 724, 726, 728, 730, 732, 734, 736, 738, 740, 742, and 744 may be captured from the social footprint. For example, determine data points 412 may use social media APIs 204 to access Facebook® or another social media site to determine that friends of person A 748 have birthday parties at 2 birthdays 724 and 3 birthdays 738. As another example, determine data points 412 may use social media APIs 204 to access Facebook® or another social media site to determine that person A 748 responded to Laura and Nick and said that he or she would go on a picnic with Laura and Nick 714.

In some embodiments, gather context data 410 may gather social media data using the social media APIs 204 and store the data in context data 126, e.g., gathered context data 608. The determine data points 412 may then examine the context data 126 and to determine that person A 748 responded to Laura and Nick 714 and said that he or she would go on a picnic with Laura and Nick 714. The determine data points 412 may send a calendar update 502 to events and engagement view of a calendar 700 with the picnic with Laura and Nick 714.

In some embodiments, the determine data points 412 may use the calendar APIs 208 to add go on a picnic with Laura and Nick 714 to events and engagement view of a calendar 700. The determine relationships 408 may determine that Laura, Nick, and person A 748 are friends or family based on going on a picnic together as well as other context data 126. Generate offers 406 may use logistic APIs 210 to book a ride from person A's 748 home (or where ever person A 748 is predicted to be) to Regent park where the picnic with Laura and Nick 714 is. The promotion and loyalty services 402 may offer promotion points if a car is selected from a particular service. Digital coupon services 404 may search for coupons to get a discount on the car ride or may look for alternative car services that have coupons that would be appropriate for the car ride to Regent park.

The determine data points 412 (or another integrated services 106) may send a calendar update 502 to events and engagement view of a calendar of both Laura and Nick. Generate offers 406 may use logistic APIs 210 to book a ride from person A's 748 home to pick-up Laura and Nick and then go to Regent park where the picnic with Laura and Nick 714 is.

In some embodiments, generate offers 406 may examine preferences 612 to determine the desired logistics of person A 748, Laura, and Nick. In some embodiment, generate offers 406 may not book the car, but get an offer for a car contingent on approval from person A 748, Laura, and Nick, e.g., generate offers 406 may send an offer message 506 to the calendars of Laura and Nick, and to the calendar of person A 748. In some embodiments, the car is not booked until person A 748, Laura, and Nick agree that they all want the car. In some embodiments, the decisions to purchase a good or service may be taken by shared members, e.g., person A 478, Laura, and Nick. In some embodiments, generate offers 406 may use user interface 104 to interact with person A 478, Laura, and Nick, and calendar APIs 208 to interact with the calendars of person A 478, Laura, and Nick, e.g., for person A 478 events and engagement view of a calendar 700. In some embodiments, generate offers 406 may generate notifications, e.g., regarding necessities or routine tasks such as haircut 720, pay rent 744, health checkups, clothing, vaccines, etc., which may be determined based on context data 126, e.g., age of person, information from person's doctor website, etc. In some embodiments, person A 748 may have typed in learn to paint 730 (or this was added based on social media posts), and the generate offers 406 may determine appropriate paint lessons (e.g., search local universities or teachers) and send an offer to person A 748 or solicit offers for person A 748 from local teachers.

Figure 8:
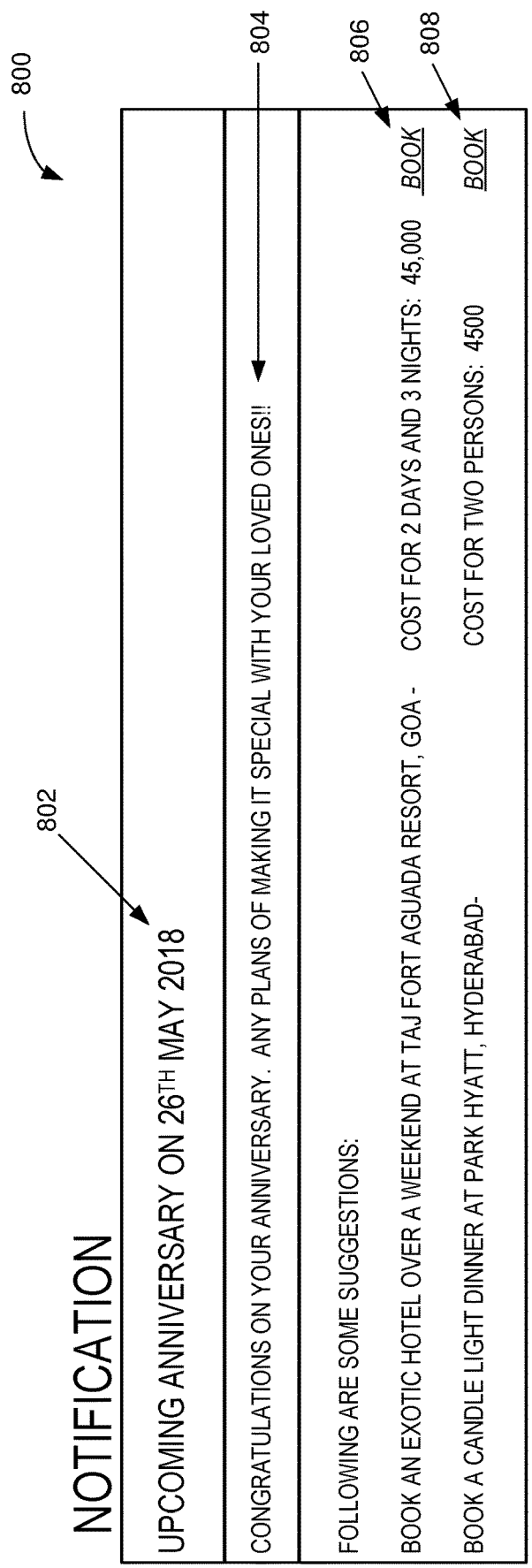
FIG. 8 illustrates a notification in accordance with some embodiments.

FIG. 8 illustrates a notification 800 in accordance with some embodiments. Illustrated in FIG. 8 is notification 800, title 802, detailed explanation 804, and list of suggestions or offers 806, 808 that includes an exotic hotel and candle light dinner. The notification 800 may be displayed on the user devices 124 of a user, e.g., person A 748. For example, generate offers 406 may send an offer message 506 using calendar APIs 208 and may use the user interface 104 to interact with person A 748. The offers 806, 808 may have been determined based on context data 126. The offer message 506 may include notifications. For example, the hotel offer 806 or dinner 808 may have been determined based on previous visits to the hotel or restaurant by person A 748 and/or the spouse (e.g., gather context data 608, e.g., using the credit card APIs 216), comments on social media by person A 748 and/or the spouse (e.g., gathered context data 608, e.g., using social media APIs 204), etc. In some embodiments, the hotel offer 806 or dinner offer 808 may be made only if there is an indication that both person A 748 and the spouse have an interest in the hotel or restaurant. The offers 806, 808 may have been determined using restaurant APIs 206 and/or ecommerce APIs 214.

Figure 9:
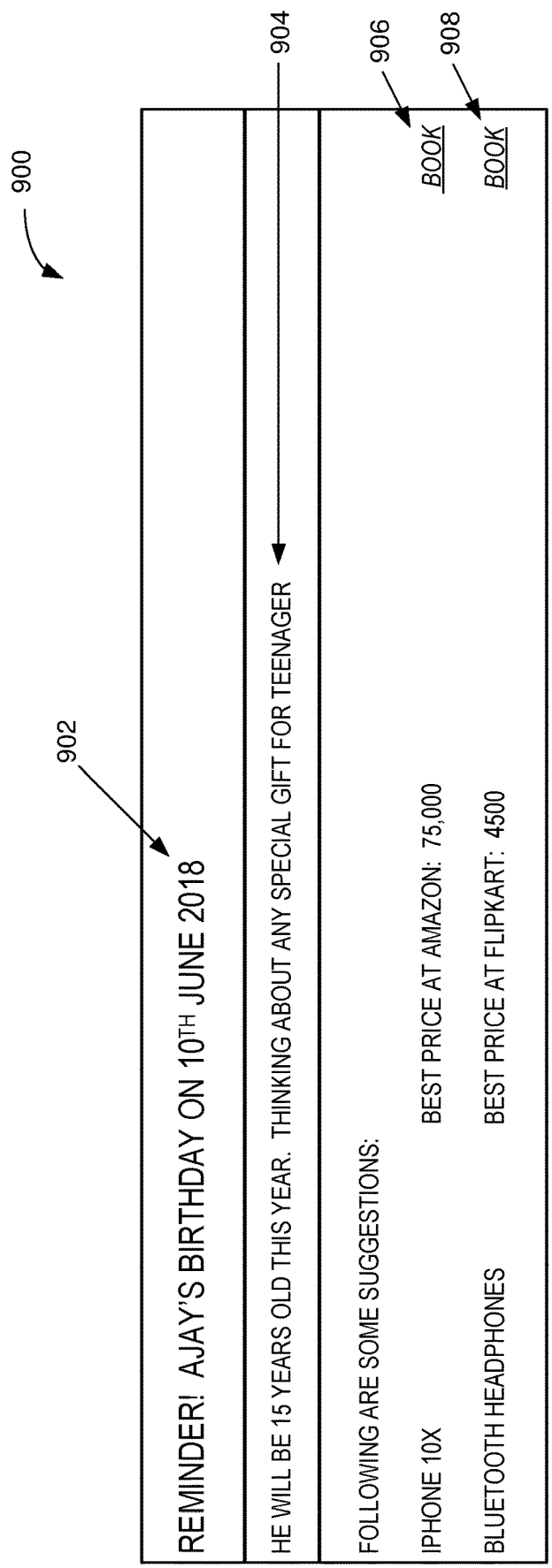
FIG. 9 illustrates a reminder in accordance with some embodiments.

FIG. 9 illustrates a reminder 900 in accordance with some embodiments. The reminder 900 may include a title 902, detailed information 904, and offers 906, 908.

The reminder 900 may be displayed on the user devices 124 of a user, e.g., person A 748. For example, generate offers 406 may send an offer message 506 using calendar APIs 208 and may use the user interface 104 to interact with person A 748. The offers 906, 908 may have been determined based on context data 126. For example, the IPhone® offer 906 or headphone offer 908 may have been determined based on an expressed desire for the offers 906, 906 by Ajay on a social media site or ecommerce site. For example, based on Ajay's social media footprint, e.g., social media APIs 304, characteristics 604 (e.g., that Ajay is at an appropriate age for a smartphone), relationships 602 (e.g., Ajay may be person A's 748 son), goods and services 616 (e.g., person A 748 may have a history of purchasing smartphones for children), etc. In some embodiments, the offers 906, 908 may only be made if there is an indication that the offer is appropriate for Ajay and person A 748, and in some embodiments, a spouse of person A 748 or additional people determined to be in a group associated with the reminder. The offers 906, 908 may have been determined using ecommerce APIs 214. The offers 906, 908 may include the hotlinks "book" (or another term such as purchase, etc.) that may take person A 748 to the site indicated in the offer 906, 908.

Figure 10:
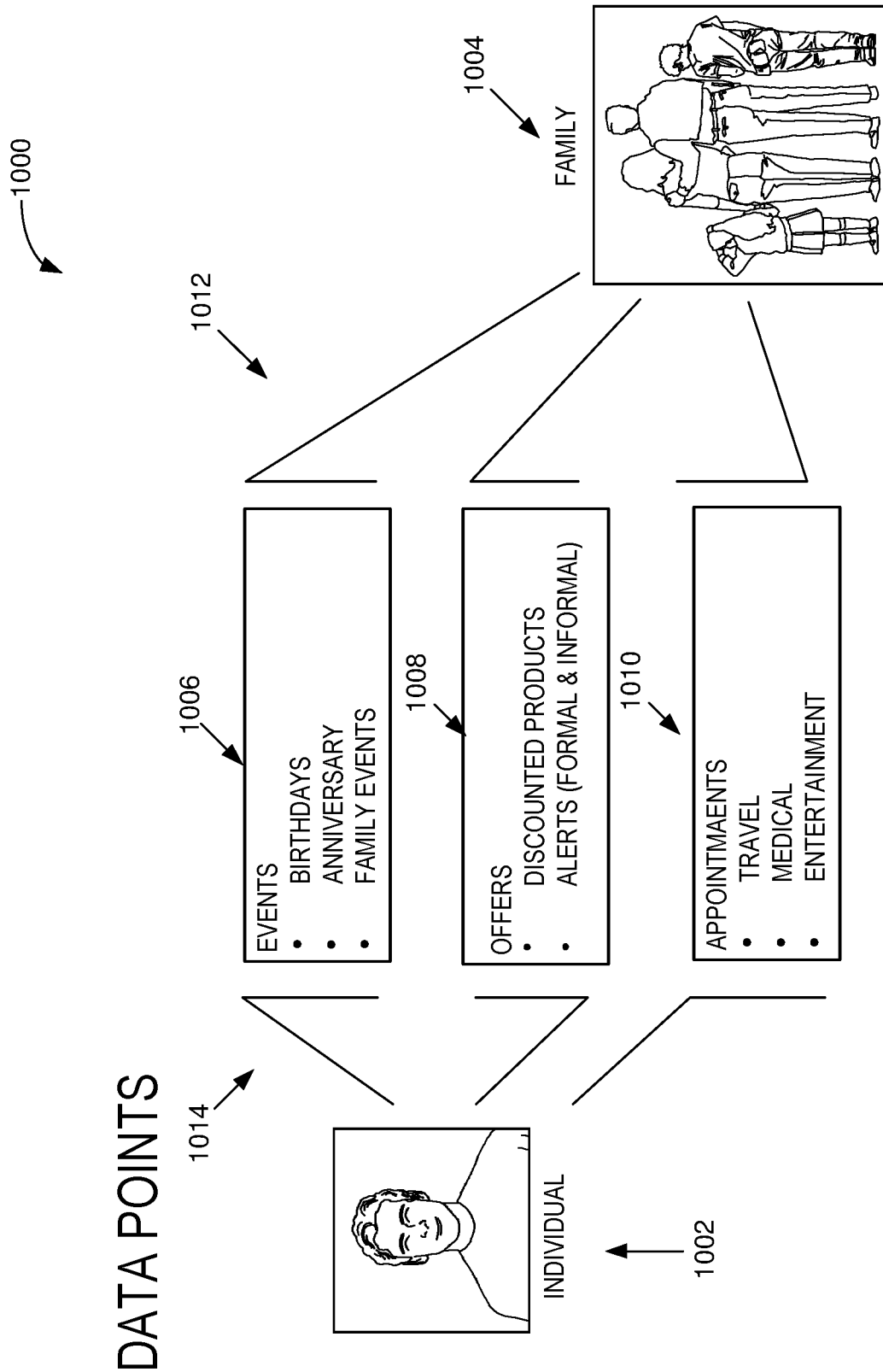
FIG. 10 illustrates data points in accordance with some embodiments.

FIG. 10 illustrates data points 1000 in accordance with some embodiments. The data points 1000 may include individual 1002, family 1004, events 1006, offers 1008, appointments 1010, and relationships 1012, 1014. The data points 1000 may be stored in context data 126, e.g., data points 610. The relationships 1012, 1014 may be determined by determine relationships 408. The offers 1008 may be determined by generate offers 406. The events 1006 and appointments 1010 may be determined by determine data points 412.

Figure 11:
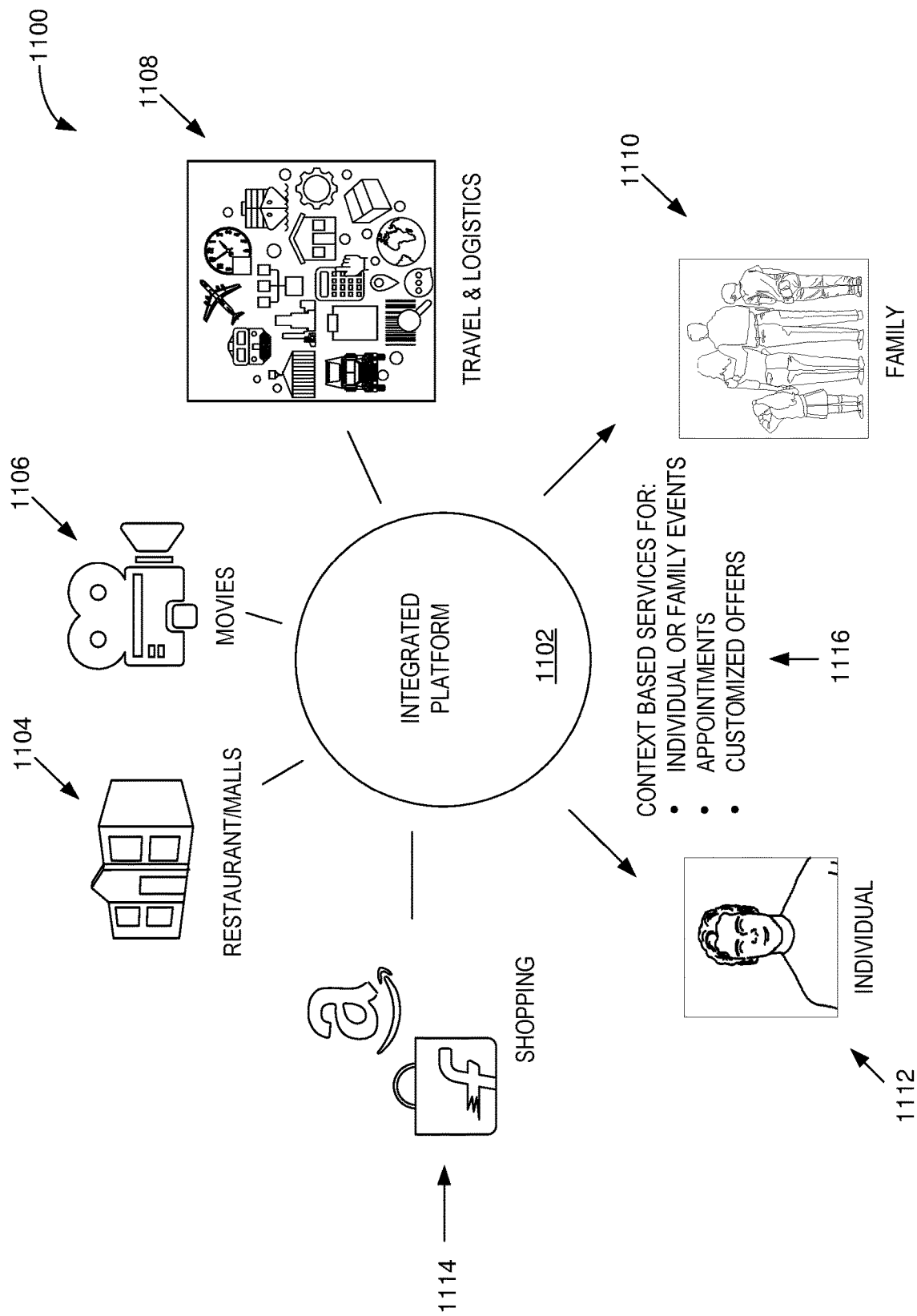
FIG. 11 illustrates an integrated platform in accordance with some embodiments.

FIG. 11 illustrates an integrated platform 1100 in accordance with some embodiments. The integrated platform 1100 is an integrated platform for aggregating context information 100 in accordance with some embodiments. Illustrated in FIG. 11 is integrated platform 1102, restaurant/malls 1104, movies 1106, travel & logistics 1108, family 1110, individual 1112, shopping 1114, and context-based services 1116.

The restaurant/malls 1104 may be determined based on platform APIs 108, e.g., restaurants APIs 206, social media APIs 204, ecommerce APIs 214, credit card APIs 216, etc. The movies 1106 may be determined based on platform APIs 108, e.g., social media AP 204, movies APIs 212, ecommerce APIs 214, and/or credit card APIs 216.

The movies 1106 may be determined based on platform APIs 108, e.g., movies APIs 212, social media APIs 204, ecommerce APIs 214, and/or credit card APIs 216. Travel & logistics 1108 may be determined based on platform APIs 108, e.g., logistics APIs 210, credit cards APIs 216, and/or social media APIs 204. Family 1110 may be determined based on platform APIs 108, e.g., social media APIs 204, calendar APIs 208, etc. The individual 1002 may be a person of people 606, e.g., person A 748. The relationships, e.g., family 1110 to individual 1112 may be determined by determine relationships 408. The data for restaurant/malls 1104, movies 1106, travel & logistics 1108, family 1110, individual 1112, shopping 1114, and context-based services 1116 may be stored in context data 126.

In accordance with some embodiments, the context-based services 1116, e.g., family events, appointments, customized offers, may be determined based on context data 126 that may be collected using platform APIs 108 and analyzed using integrated services 106.

Figure 12:
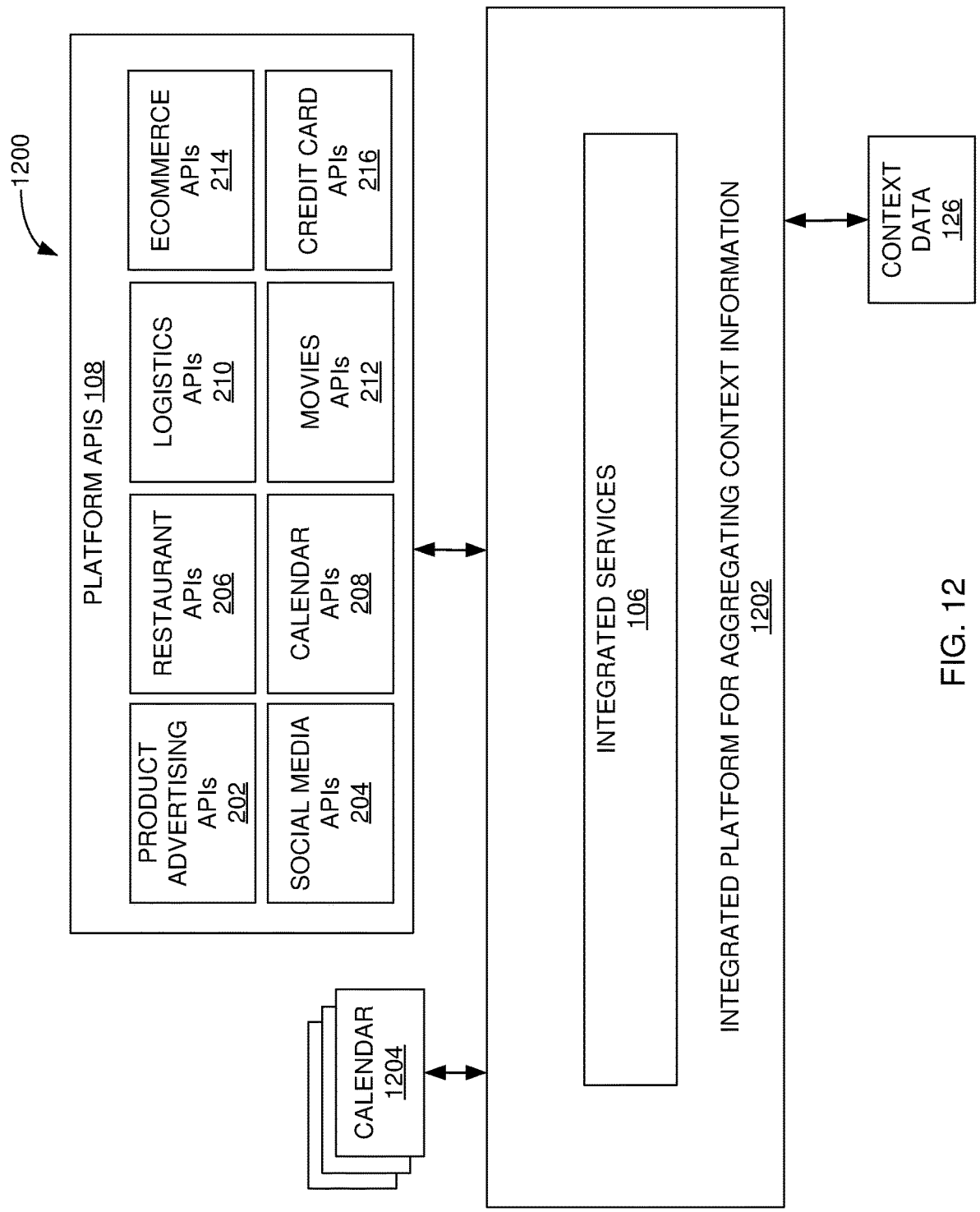
FIG. 12 illustrates a system with a support platform in accordance to some embodiments.

FIG. 12 illustrates a system with a support platform 1200 in accordance to some embodiments. The integrated platform for aggregating context information 1202 may be an ODSP™ in accordance with some embodiments. The integrated platform for aggregating context information 1202 may include integrated services 106 as disclosed herein. The integrated platform for aggregating context information 1202 may interact with calendars 1204, e.g., Google® calendars, context data 126, and platform APIs 108 as disclosed herein. The integrated platform for aggregating context information 1202 may store and retrieve context data 126 as disclosed herein. The integrated platform for aggregating context information 1202 may be configured to (i) execute on a hardware processor, (ii) extract information from social media sites using application program interfaces of the social media sites (e.g., 204), (iii) determine an event based on the extracted information (e.g., context data 126), (iv) determine a group of people (e.g., context data 126) associated with the event based on the extracted information, (v) generate an offer based on the group of people and the event, and (vi) cause the offer to be displayed (e.g., user devices 124) to at least one person of the group of people.

Figure 13:
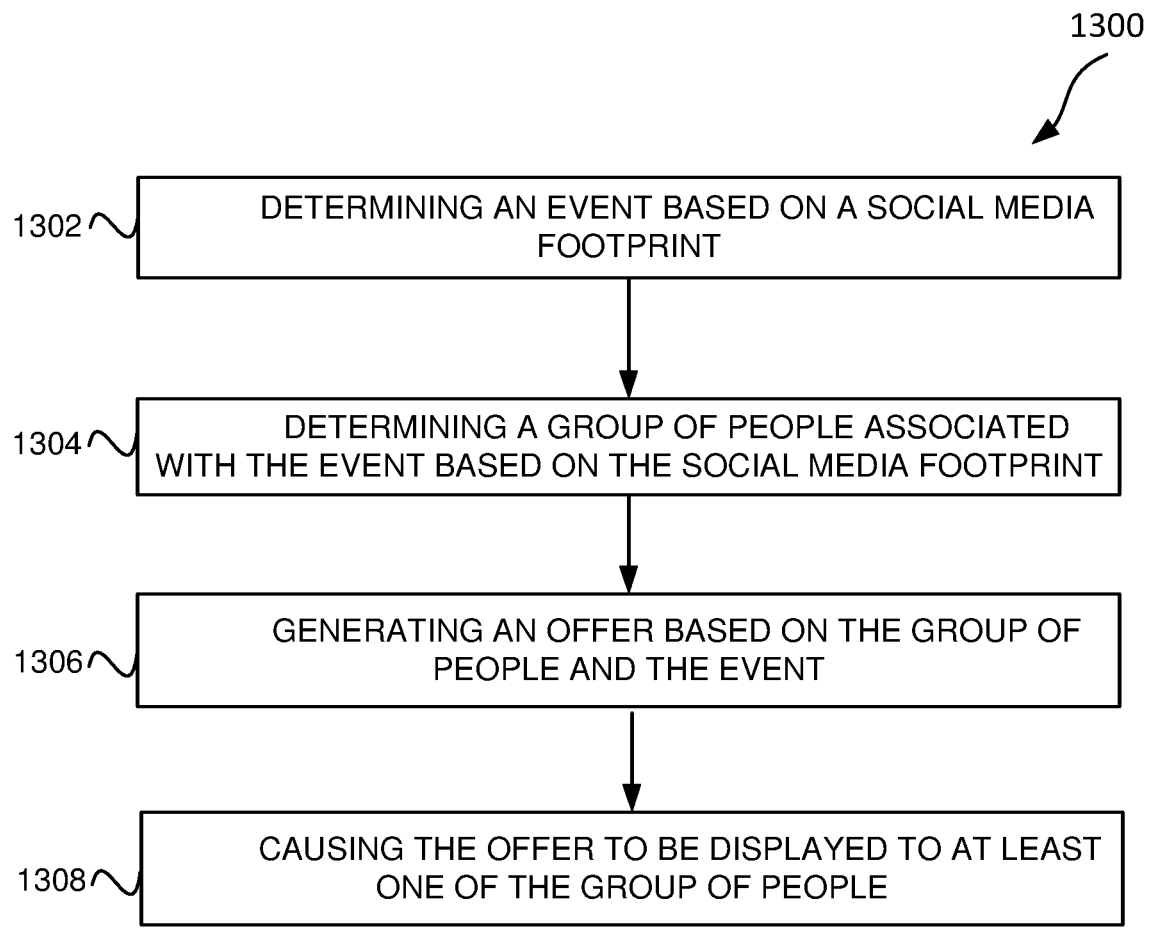
FIG. 13 illustrates a method performed on an integrated platform for aggregating context information in accordance with some embodiments.

FIG. 13 illustrates a method 1300 performed on an integrated platform for aggregating context information in accordance with some embodiments. The integrated platform for aggregating context information may be integrated platform for aggregating context information 1202, integrated platform 1102, or support platform 102. The method 1300 begins with at operation 1302 with determining an event based on a social media footprint. For example, determine data points 412 may determine an event based on context data 126 (e.g., gathered context data 608). The method 1300 continues at operation 1304 with determining a group of people associated with the event based on the social media footprint. For example, determine relationships 408 may determine the group of people based on context data 126 (e.g., people 606, relationships 602, and/or gathered context data 608).

The method 1300 may continue at operation 1306 with generating an offer based on the group of people and the event. For example, generate offers 406 may generate an offer based on context data 126 (e.g., people 606, preferences 612, and/or goods and services 616). The method 1300 may continue at operation 1308 with causing the offer to be displayed to at least one of the group of people. For example, user interface 104 may cause an offer to be displayed on user devices 124 across the network 120.

Figure 14:
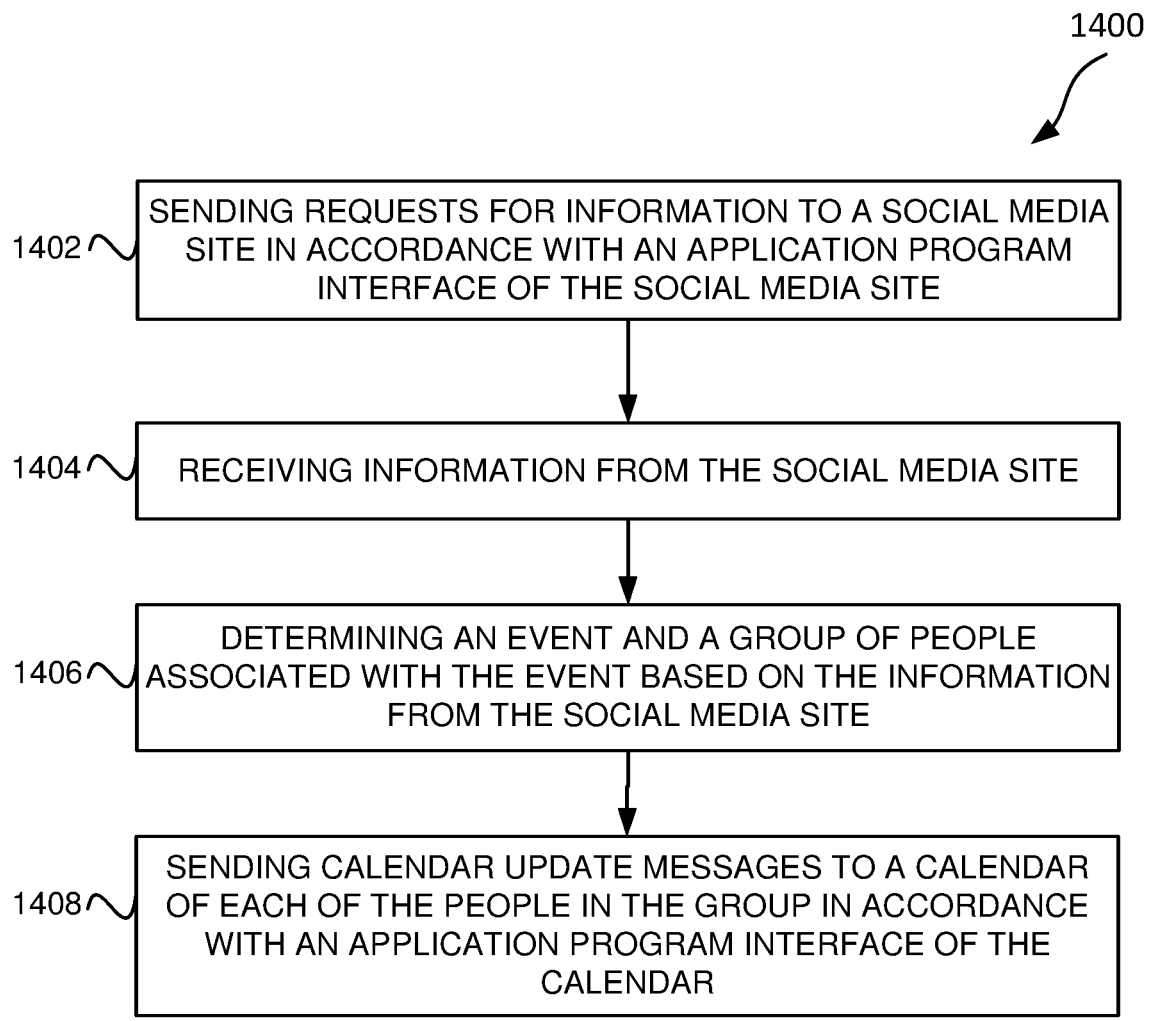
FIG. 14 illustrates a method performed on an integrated platform for aggregating context information in accordance with some embodiments.

FIG. 14 illustrates a method 1400 performed on an integrated platform for aggregating context information in accordance with some embodiments. The integrated platform for aggregating context information may be integrated platform for aggregating context information 1202, integrated platform 1102, or support platform 102. The method 1400 may begin at operation 1402 with sending requests for information to a social media site in accordance with an application program interface of the social media site. For example, gather context data 410 may send message gather data 524 to a social media site in accordance with social media APIs 204 where the social media site may use social media APIs 304.

The method 1400 may continue at operation 1404 with receiving information from the social media site. For example, support platform 102 may receive social media information 510 from the social media site over network 120. The method 1400 may continue at operation 1406 with determining an event and a group of people associated with the event based on the information from the social media site. For example, determine data points 412 may determine the event based on the context data 126 (e.g., gather context data 608). The method 1400 may continue at operation 1408 with sending calendar update messages to a calendar of each of the people in the group in accordance with an application program interface of the calendar. For example, support platform 102 may send message calendar update 502 over the network 120 to each of the people (e.g., people 606) in accordance with calendar APIs 208.

Figure 15:
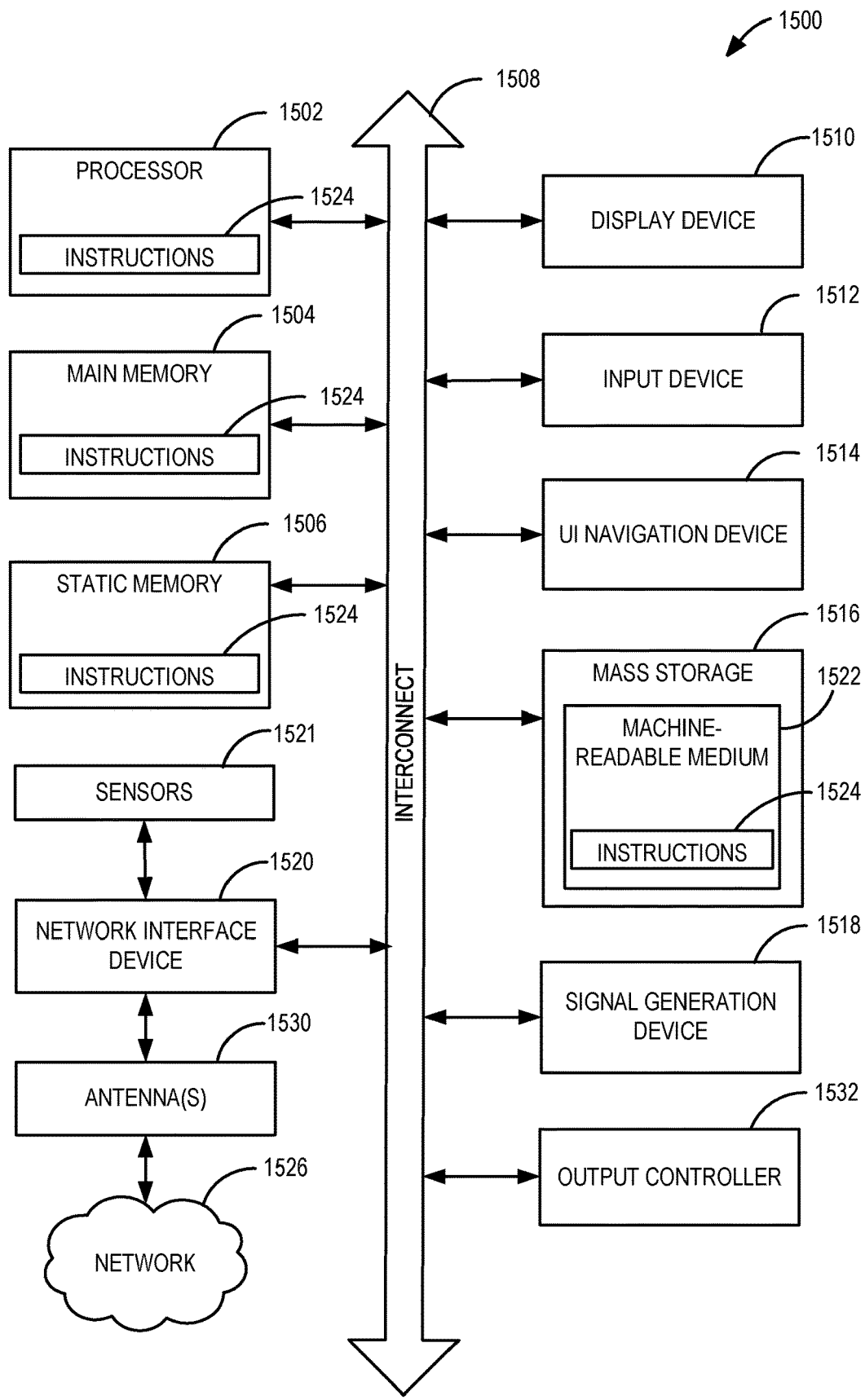
FIG. 15 illustrates a block diagram of an example machine upon which any one or more of the techniques (e.g., methodologies) discussed herein may perform.

FIG. 15 illustrates a block diagram of an example machine 1500 upon which any one or more of the techniques (e.g., methodologies) discussed herein may perform. In alternative embodiments, the machine 1500 may operate as a standalone device or may be connected (e.g., networked) to other machines. In a networked deployment, the machine 1500 may operate in the capacity of a server machine, a client machine, or both in server-client network environments. In an example, the machine 1500 may act as a peer machine in peer-to-peer (P2P) (or other distributed) network environment. The machine 1500 may be a server, personal computer (PC), a tablet PC, a set-top box (STB), a personal digital assistant (PDA), a portable communications device, a mobile telephone, a smart phone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1500 may include a hardware processor 1502 (e.g., a central processing unit (CPU), a graphics processing unit (GPU), a hardware processor core, or any combination thereof), a main memory 1504 and a static memory 1506, some or all of which may communicate with each other via an interlink (e.g., bus) 1508.

Specific examples of main memory 1504 include Random Access Memory (RAM), and semiconductor memory devices, which may include, in some embodiments, storage locations in semiconductors such as registers. Specific examples of static memory 1506 include non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; RAM; and CD-ROM and DVD-ROM disks.

The machine 1500 may further include a display device 1510, an input device 1512 (e.g., a keyboard), and a user interface (UI) navigation device 1514 (e.g., a mouse). In an example, the display device 1510, input device 1512 and UI navigation device 1514 may be a touch screen display. The machine 1500 may additionally include a mass storage (e.g., drive unit) 1516, a signal generation device 1518 (e.g., a speaker), a network interface device 1520, and one or more sensors 1521, such as a global positioning system (GPS) sensor, compass, accelerometer, or other sensor. The machine 1500 may include an output controller 1532, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.). In some embodiments the processor 1502 and/or instructions 1524 may comprise processing circuitry and/or transceiver circuitry.

The storage device 1516 may include a machine readable medium 1522 on which is stored one or more sets of data structures or instructions 1524 (e.g., software) embodying or utilized by any one or more of the techniques or functions described herein. The instructions 1524 may also reside, completely or at least partially, within the main memory 1504, within static memory 1506, or within the hardware processor 1502 during execution thereof by the machine 1500. In an example, one or any combination of the hardware processor 1502, the main memory 1504, the static memory 1506, or the storage device 1516 may constitute machine readable media.

Specific examples of machine readable media may include: non-volatile memory, such as semiconductor memory devices (e.g., EPROM or EEPROM) and flash memory devices; magnetic disks, such as internal hard disks and removable disks; magneto-optical disks; RAM; and CD-ROM and DVD-ROM disks.

While the machine readable medium 1522 is illustrated as a single medium, the term "machine readable medium" may include a single medium or multiple media (e.g., a centralized or distributed database, and/or associated caches and servers) configured to store the one or more instructions 1524.

The instructions 1524 may further be transmitted or received over a communications network 1526 using a transmission medium via the network interface device 1520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.15 family of standards known as Wi-Fi®, IEEE 802.16 family of standards known as WiMax®), IEEE 802.15.4 family of standards, a Long Term Evolution (LTE) family of standards, a Universal Mobile Telecommunications System (UMTS) family of standards, peer-to-peer (P2P) networks, among others.

In an example, the network interface device 1520 may include one or more physical jacks (e.g., Ethernet, coaxial, or phone jacks) or one or more antennas to connect to the communications network 1526. In an example, the network interface device 1520 may include one or more antennas 1530 to wirelessly communicate using at least one of single-input multiple-output (SIMO), multiple-input multiple-output (MIMO), or multiple-input single-output (MISO) techniques. In some examples, the network interface device 1520 may wirelessly communicate using Multiple User MIMO techniques. The term "transmission medium" shall be taken to include any intangible medium that is capable of storing, encoding or carrying instructions for execution by the machine 1500, and includes digital or analog communications signals or other intangible medium to facilitate communication of such software.

It should be appreciated that where software is described in a particular form (such as a component or module) this is merely to aid understanding and is not intended to limit how software that implements those functions may be architected or structured. For example, modules are illustrated as separate modules, but may be implemented as homogenous code, as individual components, some, but not all of these modules may be combined, or the functions may be implemented in software structured in any other convenient manner.

Furthermore, although the software modules are illustrated as executing on one piece of hardware, the software may be distributed over multiple processors or in any other convenient manner.

The above description is illustrative, and not restrictive. Many other embodiments will be apparent to those of skill in the art upon reviewing the above description. The scope of embodiments should therefore be determined with reference to the appended claims, along with the full scope of equivalents to which such claims are entitled.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus, the following claims are hereby incorporated into the Description of the Embodiments, with each claim standing on its own as a separate exemplary embodiment.

What is claimed is:

1. A computer-implemented method, comprising:
    determining, by at least one hardware processor, a single event based on a social media footprint;
        determining, by at least one hardware processor, a group of people to participate in the single event together based on the social media footprint, wherein the group of people comprises at least two people;
        determining, by at least one hardware processor, a service or product need for the single event based on the group of people and the single event;
    soliciting, by at least one hardware processor, offers from one or more service or product providers for the service or product;
    determining, by at least one hardware processor, an offer based on the offers from the one or more service or product providers;
    causing, by at least one hardware processor, the offer to be displayed to each person of the group of people;
        in response to receiving an acceptance of the offer from each person of the group of people, causing an acceptance of the offer to be sent to a service or product provider and accessing a calendar application program interface to add the single event to a calendar of each person of the group of people;
        in response to receiving a rejection of the offer by a person of the group of people, causing a rejection of the offer to be sent to the service or product provider; and
        in response to not receiving the acceptance of the offer from each person of the group of people, causing a rejection of the offer to be sent to the service or product provider.

2. The computer-implemented method of claim 1, further comprising:
    determining a time for a logistics booking based on a time of the single event and a cost of the logistics booking at the time, wherein the cost of the logistics booking varies depending on the time;
    generating the logistics booking prior to the single event; and
    causing the logistics booking to be transmitted to a logistics provider at the determined time.

3. The computer-implemented method of claim 1, further comprising:
    accessing an application program interface of an ecommerce site to access a shopping history of another person of the group of people;
    determine a suitable offer for the single event additionally based on the shopping history; and
    causing the suitable offer to be displayed to at least the another person of the group of people.

4. The computer-implemented method of claim 1, wherein the social media footprint comprises one or more of the following group: a credit card purchase history, information from a social media page, a purchase history of a service provider, a purchase history of a product provider, a purchase history of an ecommerce site, a purchase history of a movie theater, a purchase history of a restaurant, and a purchase history of a logistics provider.

5. The computer-implemented method of claim 1, further comprising:
accessing an application program interface of a social media site to access a friend list for one or more of the people of the group of people; and
determining the group of people based at least on the friend list.

6. The computer-implemented method of claim 1, wherein the event is one of the following: a birthday, an anniversary, a family event, and a holiday.

7. A computer-implemented method, comprising:
sending, by at least one hardware processor, requests for information to a social media site in accordance with an application program interface of the social media site;
receiving, by at least one hardware processor, information from the social media site;
determining, by at least one hardware processor, a single event and a group of people based on the information from the social media site, wherein the group of people are to participate in the single event;
determining a good or a service based on the single event and the group of people;
sending across a network requests for information regarding the good or the service to goods and services sites in accordance with another application program interface of the goods or services sites;
receiving information regarding the good or the service from the goods or services sites;
sending across a network an offer that includes the good or the service to each of the people of the group, wherein the offer for the good or service is in accordance with an application program interface of a calendar and wherein the offer includes a hotlink to one of the goods and services sites;
sending, by at least one hardware processor, calendar update messages to a calendar of each of the people in the group in accordance with an application program interface of the calendar;
in response to receiving an acceptance of the event from each person of the group of people, causing a confirmation of the event to be sent to the calendar of each person in the group and causing an acceptance of the offer to be sent to the service or product provider; and
in response to not receiving the acceptance of the offer from each person of the group of people, causing a rejection of the offer to be sent to the service or product provider.

8. The computer-implemented method of claim 7, further comprising:
sending across a network requests for information for a person of the group of people to a heath care provider site in accordance with another application program interface of the health care provider site;
receiving information from the health care provider site;
determining a health appointment is needed for the person based on the information from the health care provider site;
sending across the network an appointment request to the health care provider site for the person in accordance with the another application program interface of the health care provider site; and
sending a calendar update to a calendar of the person across the network in accordance with the calendar application program interface.

9. A system, comprising:
a server having at least one hardware processor;
an integrated platform for aggregating context information, the integrated platform for aggregating context information configured to: (i) execute on the hardware processor, (ii) extract information from social media sites using application program interfaces of the social media sites, (iii) determine a single event based on the extracted information, (iva) determine a group of people to participate in the single event based on the extracted information, wherein the group of people comprises at least two people (ivb) determine a service or product need for the event based on the group of people and the single event, (ivc) solicit offers from one or more service or product providers for the service or product, (v) determine an offer based on the offers from the one or more service or product providers, and (vi) cause the offer to be displayed to each person of the group of people; (va) in response to receiving an acceptance of the offer from each person of the group of people, causing an acceptance of the offer to be sent to a service or product provider, and causing a confirmation of the offer to be sent to a calendar of each person in the group; and (vb) in response to not receiving the acceptance of the offer from each person of the group of people, causing a rejection of the offer to be sent to the service or product provider.

10. The system of claim 9, wherein the integrated platform for aggregating context information is further configured to: (vii) send a message across a network to the calendar application of each person of the group of people, wherein the message is configured in accordance with an application program interface of the calendar and the message indicates to the calendar of each person to display the offer to the each person, and wherein the message includes a hotlink for each person to accept the offer.

11. The system of claim 9, wherein the integrated platform for aggregating context information is further configured to: (vi) store the information from the social media site in a context data storage.

12. The system of claim 9, wherein the integrated platform for aggregating context information is further configured to: (vi) access an application program interface of an ecommerce site to access a shopping history of another person of the group of people; (vii) determine the offer for the event further based on the shopping history; and (viii) send a message across a network to the calendar application of each person of the group of people, wherein the message is configured in accordance with an application program interface of the calendar and the message indicates to the calendar of each person to display the offer to each person, and wherein the message includes a hotlink for the one person to accept the offer from the ecommerce site.

13. The system of claim 9, wherein the integrated platform for aggregating context information is further configured to: (vi) access an application program interface of a social media site to access a friend list for one or more of the people of the group of people, and (vii) determine the group of people based at least on the friend list.

* * * * *